United States Patent
Herzog

(10) Patent No.: US 7,147,841 B2
(45) Date of Patent: Dec. 12, 2006

(54) FORMULATION OF UV ABSORBERS BY INCORPORATION IN SOLID LIPID NANOPARTICLES

(75) Inventor: Bernd Herzog, Grenzach-Wyhlen (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 522 days.

(21) Appl. No.: 10/460,945

(22) Filed: Jun. 13, 2003

(65) Prior Publication Data

US 2003/0235540 A1    Dec. 25, 2003

(30) Foreign Application Priority Data

Jun. 17, 2002  (EP) .................................. 02405497

(51) Int. Cl.
*A61Q 17/04* (2006.01)
*A61Q 17/00* (2006.01)
*A61Q 19/00* (2006.01)
*A61K 8/00* (2006.01)
*A61K 8/02* (2006.01)
*A61K 9/127* (2006.01)

(52) U.S. Cl. .................. 424/59; 424/60; 424/400; 424/401; 424/450

(58) Field of Classification Search ............... 424/59, 424/60, 400, 401, 450
See application file for complete search history.

(56) References Cited

U.S. PATENT DOCUMENTS

| 5,733,531 | A | 3/1998 | Mitchnick et al. ............ 424/59 |
| 5,997,888 | A | 12/1999 | Weder et al. ............... 424/401 |
| 6,294,157 | B1 * | 9/2001 | Rubinstenn et al. .......... 424/59 |
| 2002/0155073 | A1 | 10/2002 | Fankhauser et al. .......... 424/59 |

FOREIGN PATENT DOCUMENTS

| DE | 10016155 | 1/2001 |
| DE | 19952410 | 5/2001 |

OTHER PUBLICATIONS

S. A. Wissing et al., Pharmazie, vol. 56, No. 10, (2001), pp. 783-786.

* cited by examiner

*Primary Examiner*—Shelley A. Dodson
(74) *Attorney, Agent, or Firm*—Kevin T. Mansfield

(57) ABSTRACT

Solid lipid nanoparticle compositions containing
(a) 1 to 40% by weight of an oil-soluble UV absorber,
(b) 20 to 98.9% by weight of a solid lipid,
(c) 0.1 to 20% by weight of an emulsifier and
(d) 0 to 40% by weight of a liquid lipid or a liquid oil-miscible UV absorber The compositions according to the invention enhance the solubility behaviour of oil-soluble UV filters in cosmetic formulations and thereby also improve their effectiveness.

12 Claims, No Drawings

FORMULATION OF UV ABSORBERS BY INCORPORATION IN SOLID LIPID NANOPARTICLES

The present invention relates to cosmetic and dermatological formulations, especially cosmetic and dermatological light-protective formulations.

The damaging action of the ultraviolet component of the sun's rays on human skin is generally known. The rays have different effects depending on their particular wavelength: UVC radiation having wavelengths <290 nm is for the most part absorbed by the ozone layer in the stratosphere and is consequently of no physiological significance. Radiation in the range from 290 to 320 nm, the so-called UVB range, is chiefly responsible for sunburn, whereas UVA in the range from 320 to 400 nm causes ageing of the skin, but in addition likewise contributes to sunburn.

Some organic UV filters, for example difficultly soluble triazine compounds, are known to have pronounced UV filter properties and to cover a broad UV spectrum.

There is an interest in enhancing the solubility behaviour of such oil-soluble UV filters in cosmetic formulations and in that way also improving their effectiveness.

Surprisingly, it has been found that certain carriers, in which the particles consist of lipid or lipid-like (lipoid) material or mixtures thereof and have a diameter of from 10 nm to 10 μm, are solid at room temperature and biologically degradable and in addition consist of components that exhibit little or no toxicity. Such so-called solid lipid nanoparticles (SLN) are able to increase the solubility of moderately soluble UV absorbers that are soluble in cosmetic oils, that is to say UV absorbers having a solubility >1%, and enable a good cosmetic formulation to be obtained.

The present invention accordingly relates to a solid lipid nanoparticle composition containing
(a) 1 to 40% by weight of an oil-soluble UV absorber,
(b) 20 to 98.9% by weight of a solid lipid,
(c) 0.1 to 20% by weight of an emulsifier and
(d) 0 to 40% by weight of a liquid lipid or a liquid oil-miscible UV absorber.

A further advantage of the incorporation of UV absorbers in solid lipid nanoparticles is that penetration of the skin by the UV absorbers is thereby reduced, resulting in a positive effect on the toxicological potential of the UV absorbers.

As UV absorbers (component a)) there come into consideration especially oil-soluble compounds, for example organic UV absorbers from the class of the
($a_1$) phenyltriazine derivatives,
($a_2$) dibenzoylmethane derivatives,
($a_3$) diphenylacrylate derivatives,
($a_4$) benzofuran derivatives,
($a_5$) polymeric UV absorbers containing one or more organosilicon radicals,
($a_6$) camphor derivatives,
($a_7$) trianilino-s-triazine derivatives,
($a_8$) phenylbenzimidazolesulfonic acid and salts thereof,
($a_9$) menthyl anthranilates,
($a_{10}$) benzotriazole derivatives,
($a_{11}$) triazones,
($a_{12}$) trisiloxane compounds and ($a_{13}$) the compound of formula

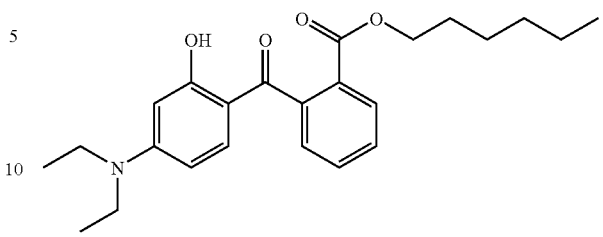

There are especially suitable as component (a):
($a_1$) p-aminobenzoic acid derivatives,
($a_{10}$) phenyltriazine derivatives,
($a_2$) dibenzoylmethane derivatives,
($a_8$) camphor derivatives,
($a_{15}$) triazones and
($a_{16}$) trisiloxane compounds.

The UV absorbers corresponding to component ($a_1$) used in the composition according to the invention are preferably compounds of formula

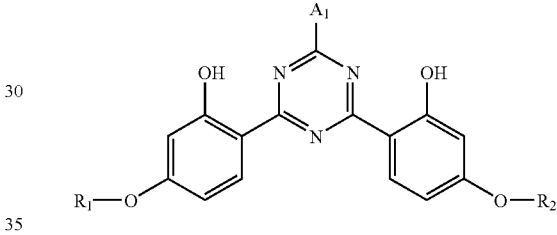

(1)

wherein
$R_1$ and $R_2$ are each independently of the other $C_1$–$C_{18}$alkyl; $C_2$–$C_{18}$alkenyl; or a radical of formula —$CH_2$—CH(—OH)—$CH_2$—O—$T_1$; or
$R_1$ and $R_2$ are a radical of formula (4a)

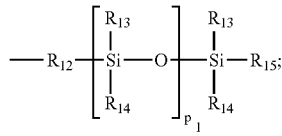

$R_{12}$ is a direct bond; a straight-chain or branched $C_1$–$C_4$alkylene radical or a radical of formula

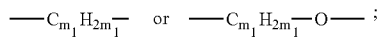

$R_{13}$, $R_{14}$ and $R_{15}$ are each independently of the others $C_1$–$C_{18}$alkyl; $C_1$–$C_{18}$alkoxy or a radical of formula

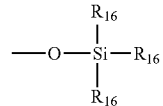

$R_{16}$ is $C_1$–$C_5$alkyl;
$m_1$ and $m_3$ are each independently of the other from 1 to 4;
$p_1$ is 0 or a number from 1 to 5;

$A_1$ is a radical of formula

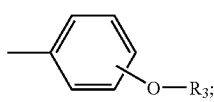 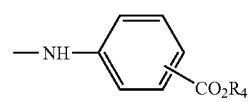

or of formula

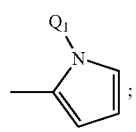

$R_3$ is hydrogen; $C_1$–$C_{10}$alkyl, —$(CH_2CHR_5$—$O)_{n_1}$—$R_4$; or a radical of formula —$CH_2$—$CH$(—$OH$)—$CH_2$—$O$—$T_1$;

$R_4$ is hydrogen; M; $C_1$–$C_5$alkyl; or a radical of formula —$(CH_2)_{m_2}$—$O$—$T_1$;

$R_5$ is hydrogen; or methyl;

$T_1$ is hydrogen; or $C_1$–$C_8$alkyl;

$Q_1$ is $C_1$–$C_{18}$alkyl;

M is a metal cation;

$m_2$ is from 1 to 4; and $n_1$ is from 1 to 16.

$C_1$–$C_5$Alkyl, $C_1$–$C_8$alkyl, $C_1$–$C_{10}$alkyl and $C_3$–$C_{18}$alkyl are straight-chain or branched alkyl radicals, e.g. methyl, ethyl, n-propyl, isopropyl, n-butyl, sec-butyl, tert-butyl, amyl, isoamyl or tert-amyl, heptyl, octyl, isooctyl, nonyl, decyl, undecyl, dodecyl, tetradecyl, pentadecyl, hexadecyl, heptadecyl or octadecyl.

$C_2$–$C_{18}$Alkenyl is, for example, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

Preference is given to bisresorcinyl compounds of formula (1) wherein $A_1$ is a radical of formula

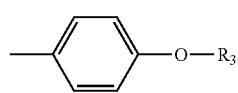 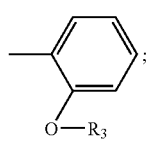

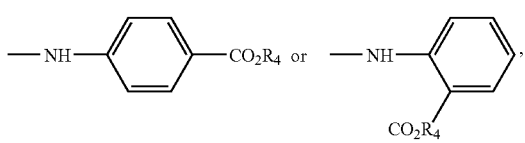

$R_3$ and $R_4$ being as defined above.

Important bisresorcinyl compounds according to the invention correspond to formula

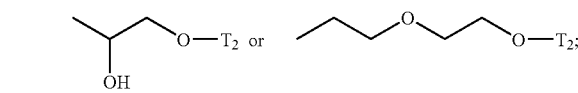

(1a)

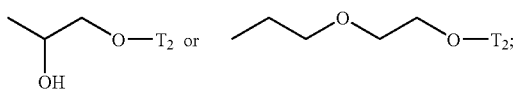

or (1b)

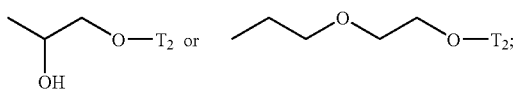

(1c)

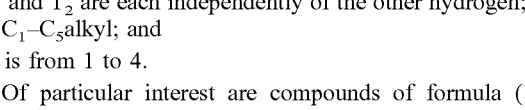

wherein $R_6$ and $R_7$ are each independently of the other $C_3$–$C_{18}$alkyl; or —$CH_2$—$CH$(—$OH$)—$CH_2$—$O$—$T_1$;

$R_8$ is $C_1$–$C_{10}$alkyl or a radical of formula

[structure showing two radicals with $T_2$]

$R_9$ is hydrogen; M; $C_1$–$C_5$alkyl; or a radical of formula —$(CH_2)_m$—$O$—$T_2$;

$T_1$ and $T_2$ are each independently of the other hydrogen; or $C_1$–$C_5$alkyl; and m is from 1 to 4.

Of particular interest are compounds of formula (1a) wherein $R_6$ and $R_7$ are each independently of the other $C_3$–$C_{18}$alkyl; or —$CH_2$—$CH$(—$OH$)—$CH_2$—$O$—$T_1$;

$R_8$ is $C_1$–$C_{10}$alkyl;

and compounds of formulae (1b) and (1c) wherein $R_6$ and $R_7$ are each independently of the other $C_3$–$C_{18}$alkyl or —$CH_2$—$CH$(—$OH$)—$CH_2$—$O$—$T_1$; and $T_1$ is hydrogen; or $C_1$–$C_5$alkyl.

Of those, special preference is given to triazine compounds of formula (1a) or (1b) wherein $R_6$ and $R_7$ have the same meaning.

The following may be mentioned as examples of compounds of formula (1):

2-(4'-methoxyphenyl)-4,6-bis(2'-hydroxy-4'-n-octyloxyphenyl)-1,3,5-triazine;

2,4-bis{[4-(3-(2-propyloxy)-2-hydroxy-propyloxy)-2-hydroxy]-phenyl}-6-(4-methoxyphenyl)-1,3,5-triazine;

2,4-bis{[4-(2-ethyl-hexyloxy)-2-hydroxy]-phenyl}-6-[4-(2-methoxyethyl-carboxyl)-phenyl-amino]-1,3,5-triazine;

2,4-bis{[4-(tris(trimethylsiloxy-silypropyloxy)-2-hydroxy]-phenyl}-6-(4-methoxyphenyl)-1,3,5-triazine;

2,4-bis{[4-(2''-methylpropenyloxy)-2-hydroxy]-phenyl}-6-(4-methoxyphenyl)-1,3,5-triazine;

2,4-bis{[4-(1',1',1',3',5',5',5'-heptamethyltrisilyl-2''-methyl-propyloxy)-2-hydroxy]-phenyl}-6-(4-methoxyphenyl)-1,3,5-triazine;

2,4-bis{[4-(3-(2-propyloxy)-2-hydroxy-propyloxy)-2-hydroxy]-phenyl}-6-[4-(ethylcarboxyl)-phenylamino]-1,3,5-triazine; and 2,4-bis{[4-(2-ethyl-hexyloxy)-2-hydroxy]-phenyl}-6-(1-methylpyrrol-2-yl)-1,3,5-triazine.

Further triazine compounds corresponding to component ($a_1$) suitable for use in accordance with the invention correspond to formula

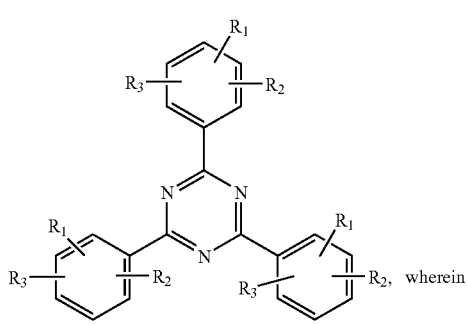

(2)

wherein $R_1$ and $R_2$ are each independently of the others hydrogen; $C_1$–$C_{12}$alkyl; or $C_1$–$C_{12}$alkoxy; and $R_3$ is $C_1$–$C_{12}$alkyl; or $C_1$–$C_{12}$alkoxy.

Of those, special preference is given to compounds of formula

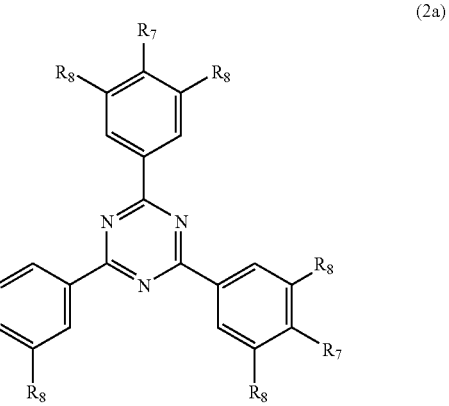

(2a)

wherein $R_7$ is $C_1$–$C_{12}$alkoxy; and $R_8$ is hydrogen; or $C_1$–$C_5$alkyl.

Very special preference is given to compounds of formula (2a) wherein $R_3$ is $C_1$–$C_{12}$alkoxy; especially methoxy; and $R_8$ is hydrogen.

The following compound is an example of a dibenzoylmethane derivative (component ($a_2$)):

butylmethoxydibenzoylmethane-[1-(4-tert-butyl)-3-(4-methoxyphenyl)propane-1,3-dione].

The following are examples of a diphenylacrylate derivatives (component $a_3$):

octocrylene (2-ethylhexyl-2-cyano-3,3'-diphenylacrylate) and etocrylene (ethyl-2-cyano-3,3'-diphenylacrylate).

The following are examples of benzofuran derivatives (component $a_4$):

3-(benzofuranyl)-2-cyanoacrylate, 2-(2-benzofuranyl)-5-tert-butylbenzoxazole and 2-(p-aminophenyl)benzofuran and, especially, the compounds of formulae

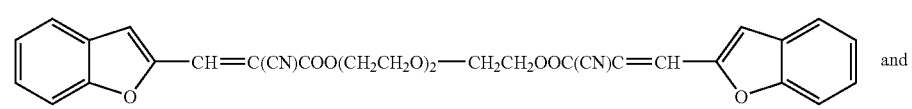 and

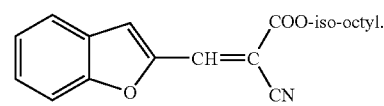

The following compounds are examples of polymeric UV absorbers that contain one or more organosilicon radicals (component $a_5$):

benzylidenemalonate derivatives, especially the compound of formula

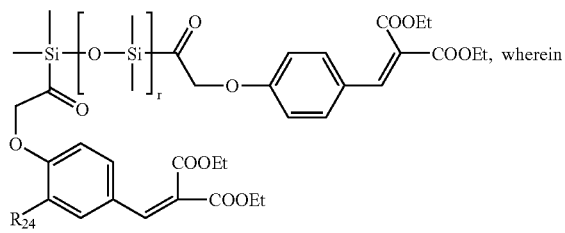

$R_{24}$ is hydrogen or methoxy and
r is about 7; the compounds of formulae

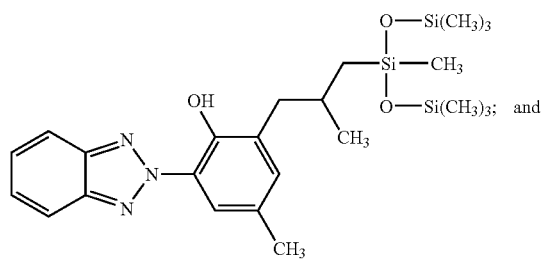

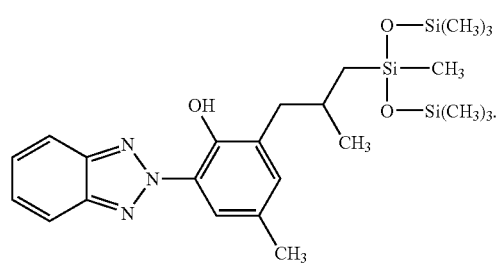

The following compounds are examples of camphor derivatives (component $a_6$):

4-methyl-benzylidenecamphor [3-(4'-methyl)benzylidene-bornan-2-one], 3-benzylidenecamphor (3-benzylidene-bornan-2-one), polyacrylamidomethylbenzylidenecamphor {N-[2(and 4)-2-oxyborn-3-ylidene-methyl)benzyl]acrylamide polymer}, trimonium-benzylidenecamphorsulfate [3-(4'-trimethylammonium)-benzylidene-bornan-2-one-methylsulfate], terephthalylidenedicamphorsulfonic acid {3,3'-(1,4-phenylenedimethine)-bis(7,7-dimethyl-2-oxobicyclo-[2.2.1] heptane-1-methanesulfonic acid} and salts thereof, and benzylidenecamphorsulfonic acid [3-(4'-sulfo)benzylidenebornan-2-one] and salts thereof.

The following compounds are examples of trianilino-s-triazine derivatives (component $a_7$):

octyltriazone-[2,4,6-trianilino-(p-carbo-2'-ethyl-1'-oxy)-1,3,5-triazine], and the trianilino-s-triazine derivatives described in U.S. Pat. No. 5,332,568, U.S. Pat. No. 5,252,323, WO 93/17002 and WO 97/03642 and EP-A-0 517 104.

The following compounds are examples of benzotriazoles (component $a_{10}$):

2-(2-hydroxy-5-methyl-phenyl)benzotriazole and compounds of formula

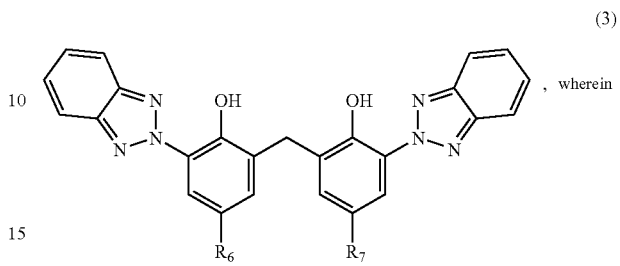

$R_6$ and $R_7$ are each independently of the other $C_1$–$C_{12}$alkyl, especially isooctyl.

Each of the above-mentioned oil-soluble UV absorbers can be used as individual compounds or in the form of mixtures with one another, such as, for example, mixtures of two, three, four, five or six of the above-mentioned UV absorbers.

The oil-soluble UV absorber or absorbers (component (a)) is/are dissolved or dispersed in the lipid or lipoid particles. It/they can also be adsorbed on the surface thereof.

The UV absorber or absorbers can be incorporated by a variety of methods:

1. Dissolution of the UV absorber in the inner phase.
2. Dissolution of the UV absorber in a solvent that is miscible with the inner phase and addition of the resulting solution to the inner phase. Some or all of the solvent is then, if desired, removed.
3. Dispersal of the UV absorber in the inner phase (e.g. by dispersal of a solid or by targeted precipitation).
4. Dissolution of the UV absorber in the lipid/lipid phase using a solubilizer (e.g. a block copolymer or sorbitan fatty acid ester) and subsequent dispersal of the lipid/lipid phase to produce the pre-dispersion.

Examples of component (b) that come into consideration are natural and synthetic triglycerides and mixtures thereof; mono- and di-glycerides on their own or mixed with one another or with, for example, triglycerides; natural and synthetic waxes, fatty alcohols, including esters and ethers thereof, and also lipid peptides.

The following, especially, are suitable: synthetic mono-, di- and tri-glycerides as individual substances or in admixture (e.g. hard fat), glycerol trifatty acid esters (e.g. glycerol trilaurate, glycerol myristate, glycerol palmitate, glycerol stearate and glycerol behenate) and waxes, e.g. cetyl palmitate and Cera alba (bleached wax, DAB 9), stearic acid, cholesterol, beeswax, and also mono-, di- and tri-glycerides of $C_{16}$–$C_{18}$ fatty acids.

Lipids and lipoids in the broadest sense, as individual compounds or in the form of mixtures, can be used as the dispersed phase.

The proportion of inner or lipid phase, based on the composition, is from 0.1 to 30% by weight and especially from 1 to 10% by weight.

The following come into consideration as emulsifiers (component (c)):

alkali metal salts, ammonium salts and amine salts of fatty acids. Examples of such salts are lithium, sodium, potassium, ammonium, triethylamine, ethanolamine, diethanolamine and triethanolamine salts. There are used especially the sodium, potassium or ammonium ($NR_1R_2R_3$) salts wherein $R_1$, $R_2$ and $R_3$ are each independently of the others hydrogen, $C_1$–$C_4$alkyl or $C_1$–$C_4$hydroxyalkyl;

saturated and unsaturated alkylsulfates, e.g. sodium dodecylsulfate, and alkanesulfonates, e.g. sodium dodecanesulfonate;

salts of bile acid, e.g. sodium cholate, sodium glycocholate and sodium taurocholate;

invert soaps (quats), e.g. cetylpyridinium chloride;

partial fatty acid esters of sorbitan, e.g. sorbitan monolaurate;

sugar esters of fatty acids, e.g. sucrose monolaurate;

alkyl glucosides, e.g. n-octyl glucoside or n-dodecyl glucoside;

alkyl maltosides, e.g. n-dodecyl maltoside;

fatty acid partial glycerides, e.g. lauric acid monoglyceride;

$C_8$–$C_{18}$betaines, $C_8$–$C_{24}$alkylamido-$C_1$–$C_4$alkylenebetaines and $C_8$–$C_{18}$sulfobetaines;

proteins, e.g. casein;

fatty acid polyglycerol esters;

fatty acid propylene glycol esters;

fatty acid lactates, e.g. sodium stearoyl-lactyl-2-lactate;

fatty alcohol phosphates

Emulsifiers of the polyoxyethylene type are more especially preferred. Examples of such emulsifiers are as follows:

polyethoxylated sorbitan fatty acid esters, e.g. polysorbate 80;

polyethoxylated fatty alcohols, e.g. oleth-20;

polyethoxylated fatty acids, e.g. polyoxyl 20 stearate;

polyethoxylated vitamin E derivatives, e.g. vitamin E polyethylene glycol 1000 succinate;

polyethoxylated lanolin and lanolin derivatives, e.g. laneth-20;

polyethoxylated fatty acid partial glycerides, e.g. diethylene glycol monostearate;

polyethoxylated alkylphenols, e.g. ethylphenol poly(ethylene glycol ether)11;

sulfuric acid semiesters of polyethoxylated fatty alcohols and salts thereof, e.g. $C_{12}$–$C_{14}$ fatty alcohol ether sulfate-2 EO-sodium salt;

polyethoxylated fatty amines and fatty acid amides;

polyethoxylated carbohydrates;

block polymers of ethylene oxide and propylene oxide, e.g. poloxamer 188.

As examples of component (d) there come into consideration, for example, cosmetic oils, such as caprylic/capric triglyceride (Miglyol 812) or UV absorbers present in the form of oil, for example ethylhexylmethoxy cinnamate, octocrylene, and Parsol SLX. Component (d) is generally optional, but must be added when the lipid/lipoid (which is solid at room temperature) has a tendency to crystallise, which might result in the displacement of the UV absorber from the solid lipid nanoparticles. A certain amount of a liquid fatty substance will prevent the crystal formation of the solid lipid/lipoid and consequently also the un-desired effect of displacement of the UV absorber from the particles.

Should the use of dispersion-stabilizing additives prove neccesary in order to produce stable dispersions, such additives can be used in the form of pure substances or in the form of mixtures to stabilize the particles. They may be present in amounts in the range from 0.01 to 20% by weight and preferably from 0.5 to 5% by weight, based on the total weight of the aqueous dispersion. Stabilizing substances that come into consideration are:

α) surfactants, especially ethoxylated sorbitan fatty acid esters, block polymers and block copolymers (e.g. poloxamers and poloxamines), polyglycerol ethers and esters, lecithins of varied origin (e.g. egg lecithin or soya lecithin), chemically modified lecithins (e.g. hydrogenated lecithin) and also phospholipids and sphingolipids, mixtures of lecithins with phospholipids, sterols (e.g. cholesterol and cholesterol derivatives and also stigmasterol), esters and ethers of sugars or sugar alcohols with fatty acids or fatty alcohols (e.g. saccharose monostearate), β) sterically stabilizing substances, such as poloxamers and poloxamines (polyoxyethylene-polyoxypropylene block polymers), ethoxylated sorbitan fatty acid esters, ethoxylated mono- and di-glycerides, ethoxylated lipids and lipoids, ethoxylated fatty alcohols or fatty acids and γ) charge stabilizers or charge carriers, e.g. dicetyl phosphate, phosphatidylglycerol and also saturated and unsaturated fatty acids, sodium cholate, sodium glycol cholate, sodium taurocholate or mixtures thereof, amino acids or peptizers, such as sodium citrate (see J. S. Lucks, B. W. Müller, R. H. Müller, Int. J. Pharmaceutics 63, 183–188 (1990))

δ) viscosity-increasing substances, such as cellulose ethers and esters (e.g. methyl cellulose, hydroxyethyl cellulose, hydroxypropyl cellulose, sodium carboxymethylcellulose), polyvinyl derivatives, such as polyvinyl alcohol, polyvinylpyrrolidone, polyvinyl acetate, alginates, polyacrylates (e.g. carbopol), xanthans and pectins.

The charge stabilizers, if required, are used preferably in an amount of from 0.01 to 10% and especially from 0.05 to 2%, relative to the base formulation, and the viscosity-increasing substances, if required, are used in an amount of from 0.01 to 10%, especially from 0.1 to 10% and more especially from 0.5 to 5%, relative to the base formulation.

Since dispersions of solid lipid nanoparticles are stable even at relatively high temperatures, they can very easily be incorporated into cosmetic and dermatological formulations by replacing a portion of the aqueous phase with the aqueous SLN dispersion. Accordingly, the combination of UV absorbers incorporated in solid lipid nanoparticles with conventionally formulated UV absorbers is likewise possible.

Preferred solid lipid nanoparticle compositions according to the invention comprise (a) a UV absorber of formula (1), (b) a synthetic mono-, di- or tri-glyceride, and (c) a fatty alcohol phosphate.

Further preferred solid lipid nanoparticle compositions according to the invention comprise (a) as UV absorber, butamidotriazone, (b) a synthetic mono-, di- or tri-glyceride, and (c) a fatty alcohol phosphate.

Solid lipid nanoparticles can be prepared in the following manner: the inner phase (the lipid or lipoid) is emulsified in the molten or softened state. Emulsification is carried out above room temperature in the continuous (generally aqueous) phase, which can contain the emulsifier or the emulsifier mixture. The emulsion droplets formed can be comminuted to the nanometer range by high-pressure homogenization. After cooling, the comminuted droplets are then present in the solid state and, as it were, frozen in that fine state, in the form of solid lipid nanoparticles.

The solid lipid nanoparticles are thus particles that are solid at room temperature (that is, about 20° C) of a size in the nanometer range. The particles can be dispersed in an aqueous medium, so that it is possible to refer to a solid/liquid dispersion. The particle size of the dispersed phase varies in the range of from >10 nm to a few micrometers (about 10 μm). The average particle size (diameter determined by photon correlation spectroscopy) is predominantly in the range from 100 to 1000 nm, especially from 100 to 800 nm. By suitable choice of the process parameters and suitable choice of adjuvants (e.g. relatively high emulsifier concentration) it is, however, possible to produce SLNs smaller than 100 nm, especially in the range from 40 to 80 nm.

The solid lipid nanoparticles are prepared according to the hot homogenization technique, which is suitable especially for the incorporation of lipophilic substances. For that purpose the lipophilic UV absorber is dissolved or finely dispersed in the lipid melt at a temperature at least 5° C. above the melting point of the lipids, whereupon the hot aqueous emulsifier solution is added and everything is mixed together using an Ultraturrax.

The pre-emulsion so obtained is homogenized in the hot state at from 250 to 1500 bar in a high-pressure homogenizer (Avestin, Emulsiflex C5). When the system is cooled, solid lipid nanoparticles form in which the lipophilic UV absorber is encapsulated.

Toxic adjuvants, for example readily volatile chlorinated hydrocarbon solvents, need not be used in the preparation process.

The composition according to the invention is suitable especially as a light-protective agent in cosmetic, dermatological, pharmaceutical and veterinary medicine preparations.

The invention relates also to a cosmetic preparation for the skin or hair comprising a solid lipid nanoparticle composition according to claim 1, and carriers or adjuvants acceptable in skin and hair cosmetics.

The cosmetic preparation contains from 10 to 80% by weight, preferably from 20 to 60% by weight, based on the total weight of the composition, of one or more UV absorbers and at least one cosmetically acceptable adjuvant.

The cosmetic preparation can be prepared by physically mixing the solid lipid nanoparticle composition with the adjuvant using customary methods, for example by simply stirring together the individual components, especially by making use of the dissolution properties of cosmetic UV absorbers that are already known, such as, for example, OMC, salicylic acid isooctyl ester etc.

The cosmetic preparation can, for example, be a cream, a gel, a lotion, an alcoholic or aqueous/alcoholic solution, emulsion, wax/fat composition, stick preparation, powder or ointment.

As water- and oil-containing emulsions (e.g. W/O, O/W, O/W/O and W/O/W emulsions or microemulsions) such preparations contain, for example, from 0.1 to 30% by weight, preferably from 20 to 60% by weight, based on the total weight of the composition, of the solid lipid nanoparticle composition, from 1 to 60% by weight, especially from 5 to 50% by weight and preferably from 10 to 35% by weight, based on the total weight of the composition, of at least one oil component, from 0 to 30% by weight, especially from 1 to 30% by weight and more especially from 4 to 20% by weight, based on the total weight of the composition, of at least one emulsifier, from 10 to 90% by weight, especially from 30 to 90% by weight, based on the total weight of the composition, of water and from 0 to 88.9% by weight, especially from 1 to 50% by weight, of further cosmetically acceptable adjuvants, and water ad 100%.

As oil components of oil-containing compositions (e.g. oils, W/O, O/W, O/W/O and W/O/W emulsions or microemulsions) there come into consideration, for example, Guerbet alcohols based on fatty alcohols having from 6 to 18, preferably from 8 to 10, carbon atoms, esters of linear $C_6$–$C_{24}$ fatty acids with linear $C_3$–$C_{24}$ alcohols, esters of branched $C_6$–$C_{13}$ carboxylic acids with linear $C_6$–$C_{24}$ fatty alcohols, esters of linear $C_6$–$C_{24}$ fatty acids with branched alcohols, especially 2-ethylhexanol, esters of hydroxycarboxylic acids with linear or branched $C_6$–$C_{22}$ fatty alcohols, especially dioctyl malate, esters of linear and/or branched fatty acids with polyhydric alcohols (for example propylene glycol, dimer diol or trimer triol) and/or Guerbet alcohols, triglycerides based on $C_6$–$C_{10}$ fatty acids, liquid mono-/di-/tri-glyceride mixtures based on $C_6$–$C_{18}$ fatty acids, esters of $C_6$–$C_{24}$ fatty alcohols and/or Guerbet alcohols with aromatic carboxylic acids, especially benzoic acid, esters of $C_2$–$C_{12}$ dicarboxylic acids with linear or branched alcohols having from 1 to 22 carbon atoms or polyols having from 2 to 10 carbon atoms and from 2 to 6 hydroxyl groups, vegetable oils (such as sunflower oil, olive oil, soybean oil, rapeseed oil, almond oil, jojoba oil, orange oil, wheatgerm oil, peach kernel oil and the liquid components of coconut oil), branched primary alcohols, substituted cyclohexanes, linear and branched $C_6$–$C_{22}$ fatty alcohol carbonates, Guerbet carbonates, esters of benzoic acid with linear and/or branched $C_6$–$C_{22}$ alcohols (e.g. Finsolv® TN), linear or branched, symmetric or asymmetric dialkyl ethers having a total of from 12 to 36 carbon atoms, especially from 12 to 24 carbon atoms, for example di-n-octyl ether, di-n-decyl ether, di-n-nonyl ether, di-n-undecyl ether, di-n-dodecyl ether, n-hexyl-n-octyl ether, n-octyl-n-decyl ether, n-decyl-n-undecyl ether, n-undecyl-n-dodecyl ether, n-hexyl-n-undecyl ether, di-tert-butyl ether, diisopentyl ether, di-3-ethyidecyl ether, tert-butyl-n-octyl ether, isopentyl-n-octyl ether and 2-methyl-pentyl-n-octyl ether; ring-opening products of epoxidised fatty acid esters with polyols; silicone oils and/or aliphatic or naphthenic hydrocarbons. Also of importance are monoesters of fatty acids with alcohols having from 3 to 24 carbon atoms. That group of substances comprises the esterification products of fatty acids having from 8 to 24 carbon atoms, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical mixtures thereof (obtained, for example, in the pressure removal of natural fats and oils, in the reduction of aldehydes from Roelen's oxosynthesis or in the dimerization of unsaturated fatty acids) with alcohols, for example, isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical mixtures thereof (obtained, for example, in the high-pressure hydrogenation of technical methyl esters based on fats and oils or aldehydes from Roelen's oxosynthesis and as monomer fractions in the dimerization of unsaturated fatty alcohols). Of special importance are isopropyl myristate, isononanoic acid $C_{16}$–$C_{18}$alkyl esters, stearic acid 2-ethylhexyl ester, cetyl oleate, glycerol tricaprylate, coconut fatty alcohol caprinate/caprylate and n-butyl stearate. Further oil components that can be used are dicarboxylic acid esters, such as di-n-butyl adipate, di(2-ethylhexyl) adipate, di(2-ethylhexyl) succinate and diisotridecyl acetate, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate. Preferred mono- or poly-ols are ethanol, isopropanol, propylene glycol, hexylene glycol, glycerol and sorbitol. It is also possible to use di- and/or tri-valent metal salts (alkaline earth metal, $Al^{3+}$ inter alia) of one or more alkylcarboxylic acids.

The oil components can be used in an amount of, for example, from 1 to 60% by weight, especially from 5 to 50% by weight and preferably from 10 to 35% by weight, based on the total weight of the composition.

Any conventionally usable emulsifier can be used for the compositions.

As emulsifiers there come into consideration, for example, non-ionic surfactants from the following groups:
  addition products of from 2 to 30 mol of ethylene oxide and/or from 0 to 5 mol of propylene oxide with linear fatty alcohols having from 8 to 22 carbon atoms, with fatty acids having from 12 to 22 carbon atoms and with alkylphenols having from 8 to 15 carbon atoms in the alkyl group, for example ceteareth-20 or ceteareth-12;
  $C_{12}$–$C_{22}$ fatty acid mono- and di-esters of addition products of from 1 to 30 mol of ethylene oxide with polyols having from 3 to 6 carbon atoms, especially with glycerol;
  glycerol mono- and di-esters and sorbitan mono- and di-esters of saturated and unsaturated fatty acids having from 6 to 22 carbon atoms and ethylene oxide addition products thereof, for example glyceryl stearate, glyceryl isostearate, glyceryl oleate, sorbitan oleate or sorbitan sesquioleate;
  $C_8$–$C_{22}$alkyl-mono- and -oligo-glycosides and ethoxylated analogues thereof, degrees of oligomerization of from 1.1 to 5, especially from 1.2 to 1.4, being preferred, and glucose being preferred as the sugar component;
  addition products of from 2 to 60 mol, especially from 15 to 60 mol, of ethylene oxide with castor oil and/or hardened castor oil;
  polyol esters and especially polyglycerol esters, for example diisostearoyl polyglyceryl-3-diisostearate, polyglyceryl-3-diisostearate, triglyceryl diisostearate, polyglyceryl-2-sesquiisostearate or polyglyceryl dimerate. Mixtures of compounds from a plurality of those substance classes are also suitable;
  partial esters based on linear, branched, unsaturated or saturated $C_6$–$C_{22}$ fatty acids, ricinoleic acid and also 12-hydroxystearic acid and on glycerol, polyglycerol, pentaerythritol, dipentaerythritol, sugar alcohols (e.g. sorbitol), alkyl glucosides (e.g. methyl glucoside, butyl glucoside, lauryl glucoside) and also polyglucosides (e.g. cellulose), for example polyglyceryl-2-dihydroxystearate or polyglyceryl-2-diricinoleate;
  mono-, di- and tri-alkylphosphates and also mono-, di- and/or tri-PEG-alkylphosphates and salts thereof;
  wool wax alcohols;
  one or more ethoxylated esters of natural derivatives, for example polyethoxylated esters of hydrogenated castor oil;
  silicone oil emulsifiers, for example silicone polyol;
  polysiloxane/polyalkylpolyether copolymers and corresponding derivatives, for example cetyl dimethicone copolyol;
  mixed esters of pentaerythritol, fatty acids, citric acid and fatty alcohol (see DE-A-1 165 574) and/or mixed esters of fatty acids having from 6 to 22 carbon atoms, methylglucose and polyols, preferably glycerol or polyglycerol, for example polyglyceryl-3-glucose distearate, polyglyceryl-3-glucose dioleate, methyl glucose dioleate or dicocoyl pentaerythryl distearyl citrate and also
  polyalkylene glycols.

The addition products of ethylene oxide and/or of propylene oxide with fatty alcohols, fatty acids, alkylphenols, glycerol mono- and di-esters and also sorbitan mono- and di-esters of fatty acids, or with castor oil, are known, commercially available products. They are usually homologue mixtures, the average degree of alkoxylation of which corresponds to the ratio of the amounts of ethylene oxide and/or propylene oxide and substrate with which the addition reaction is carried out. $C_{12}$–$C_{18}$ fatty acid mono- and di-esters of addition products of ethylene oxide with glycerol are known, for example, from DE-A-2 024 051 as fat-restoring substances for cosmetic preparations.

$C_8$–$C_{18}$Alkyl-mono- and -oligo-glycosides, their preparation and their use are known from the prior art. They are prepared especially by reacting glucose or oligosaccharides with primary alcohols having from 8 to 18 carbon atoms. Suitable glycoside radicals include monoglycosides in which a cyclic sugar radical is glycosidically bonded to the fatty alcohol and also oligomeric glycosides having a degree of oligomerization of up to preferably about 8. The degree of oligomerization is a statistical average value based on a homologue distribution customary for such technical products.

It is also possible to use zwitterionic surfactants as emulsifiers. The term "zwitterionic surfactants" denotes especially surface-active compounds that carry at least one quaternary ammonium group and at least one carboxylate and/or sulfonate group in the molecule. Zwitterionic surfactants that are especially suitable are the so-called betaines, such as N-alkyl-N,N-dimethylammonium glycinates, for example cocoalkyldimethylammonium glycinate, N-acylaminopropyl-N,N-dimethylammonium glycinates, for example cocoacylaminopropyl-dimethylammonium glycinate, and 2-alkyl-3-carboxymethyl-3-hydroxyethylimidazolines each having from 8 to 18 carbon atoms in the alkyl or acyl group and also cocoacylaminoethylhydroxyethylcarboxymethylglycinate. Special preference is given to the fatty acid amide derivative known by the CTFA name cocamidopropyl betaine. Likewise suitable as emulsifiers are ampholytic surfactants. Ampholytic surfactants are to be understood as meaning especially those which, in addition to containing a $C_8$–$C_{18}$-alkyl or -acyl group, contain at least one free amino group and at least one —COOH or —$SO_3H$ group in the molecule and are capable of forming internal salts. Examples of suitable ampholytic surfactants include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each having approximately from 8 to 18 carbon atoms in the alkyl group. Ampholytic surfactants to which special preference is given are N-cocoalkylaminopropionate, cocoacylaminoethylaminopropionate and $C_{12}$–$C_{18}$acylsarcosine. In addition to the ampholytic emulsifiers there also come into consideration quaternary emulsifiers, special preference being given to those of the esterquat type, preferably methyl-quaternised difatty acid triethanolamine ester salts.

Non-ionic emulsifiers are preferred. Of the non-ionic emulsifiers mentioned, special preference is given to ethoxylated fatty alcohols having from 8 to 22 carbon atoms and from 4 to 30 EO units.

The emulsifiers may be used in an amount of, for example, from 1 to 30% by weight, especially from 4 to 20% by weight and preferably from 5 to 10% by weight, based on the total weight of the composition. It is, however, also possible in principle to dispense with the use of emulsifiers.

The preparations according to the invention, for example creams, gels, lotions, alcoholic and aqueous/alcoholic solutions, emulsions, wax/fat compositions, stick preparations, powders or ointments, may in addition contain, as further adjuvants and additives, mild surfactants, super-fatting agents, pearlescent waxes, consistency regulators, thickeners, polymers, silicone compounds, fats, waxes, stabilizers, biogenic active ingredients, deodorising active ingredients, anti-dandruff agents, film formers, swelling agents, further UV light-protective factors, antioxidants, hydrotropic agents, preservatives, insect repellents, self-tanning agents, solubilizers, perfume oils, colorants, bacteria-inhibiting agents and the like. Substances suitable for use as super-fatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilizers.

Examples of suitable mild surfactants, that is to say surfactants especially well tolerated by the skin, include fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, α-olefin sulfonates, ethercarboxylic acids, alkyl oligoglucosides, fatty acid glucamides, alkylamidobetaines and/or protein fatty acid condensation products, the latter preferably being based on wheat proteins.

As pearlescent waxes there come into consideration, for example: alkylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially laurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxyl groups, and mixtures thereof.

As consistency regulators there come into consideration especially fatty alcohols or hydroxy fatty alcohols having from 12 to 22 carbon atoms and preferably from 16 to 18 carbon atoms, and in addition partial glycerides, fatty acids and hydroxy fatty acids. Preference is given to a combination of such substances with alkyl-oligoglucosides and/or fatty acid N-methylglucamides of identical chain length and/or polyglycerol poly-12-hydroxystearates. Suitable thickeners include, for example, Aerosil types (hydrophilic silicic acids), polysaccharides, especially xanthane gum, guar-guar, agar-agar, alginates and Tyloses, carboxymethyl cellulose and hydroxymethyl cellulose, also high-molecular-weight polyethylene glycol mono- and di-esters of fatty acids, polyacrylates (e.g. Carbopol® from Goodrich or Synthalen® from Sigma), polyacrylamides, polyvinyl alcohol and polyvinylpyrrolidone, surfactants, for example ethoxylated fatty acid glycerides, esters of fatty acids with polyols, for example pentaerythritol or trimethylolpropane, fatty alcohol ethoxylates with restricted homologue distribution and alkyloligoglucosides as well as electrolytes, such as sodium chloride or ammonium chloride.

Suitable cationic polymers are, for example, cationic cellulose derivatives, for example a quaternised hydroxymethyl cellulose obtainable under the name Polymer JR 400® from Amerchol, cationic starch, copolymers of diallylammonium salts and acrylamides, quaternised vinylpyrrolidone/vinyl imidazole polymers, for example Luviquat® (BASF), condensation products of polyglycols and amines, quaternised collagen polypeptides, for example lauryldimonium hydroxypropyl hydrolyzed collagen (Lamequat®L/Grünau), quaternised wheat polypeptides, polyethyleneimine, cationic silicone polymers, for example amidomethicones, copolymers of adipic acid and dimethylaminohydroxypropyldiethylenetriamine (Cartaretin®/Sandoz), copolymers of acrylic acid with dimethyldiallylammonium chloride (Merquat® 550/Chemviron), polyaminopolyamides, as described, for example, in FR-A-2 252 840, and the crosslinked water-soluble polymers thereof, cationic chitin derivatives, for example quaternised chitosan, optionally distributed in microcrystalline form; condensation products of dihaloalkyls, for example dibromobutane, with bisdialkylamines, for example bisdimethylamino-1,3-propane, cationic guar gum, for example Jaguar® C-17, Jaguar® C-16 from Celanese, quaternised ammonium salt polymers, for example Mirapol® A-15, Mirapol® AD-1, Mirapol® AZ-1 from Miranol.

As anionic, zwitterionic, amphoteric and non-ionic polymers there come into consideration, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyltrimethylammonium chloride/acrylate copolymers, octyl acrylamide/methyl methacrylate/tert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinyl caprolactam terpolymers and also cellulose ethers and silicones which may or may not be derivatised.

Suitable silicone compounds are, for example, dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Also suitable are simethicones, which are mixtures of dimethicones having an average chain length of from 200 to 300 dimethylsiloxane units with hydrogenated silicates. A detailed survey by Todd et al. of suitable volatile silicones may also be found in Cosm. Toil. 91, 27 (1976).

Typical examples of fats are glycerides, and as waxes there come into consideration, inter alia, beeswax, carnauba wax, candelilla wax, montan wax, paraffin wax, hydrogenated castor oils and fatty acid esters or microwaxes solid at room temperature optionally in combination with hydrophilic waxes, e.g. cetylstearyl alcohol or partial glycerides. Metal salts of fatty acids, for example magnesium, aluminium and/or zinc stearate or ricinoleate, may be used as stabilizers.

Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

As deodorising active ingredients there come into consideration, for example, antiperspirants, for example aluminium chlorohydrates (see J. Soc. Cosm. Chem. 24, 281 (1973)). For example an aluminium chlorohydrate corresponding to formula $Al_2(OH)_5Cl \times 2.5\ H_2O$ is available commercially under the trade mark Locron® of Hoechst AG, Frankfurt (FRG), and the use thereof is especially preferred (see J. Pharm. Pharmacol. 26, 531 (1975)). Besides the chlorohydrates, it is also possible to use aluminium hydroxyacetates and acidic aluminium/zirconium salts. Esterase inhibitors may be added as further deodorising active ingredients. Such inhibitors are preferably trialkyl citrates, such as trimethyl citrate, tripropyl citrate, triisopropyl citrate, tributyl citrate and especially triethyl citrate (Hydagen® CAT, Henkel KGaA, Düsseldorf/FRG), which inhibit enzyme activity and hence reduce the development of odour. Further substances that come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that affect the germ flora and kill or inhibit the growth of sweat-decomposing bacteria can likewise be present in the preparations (especially in stick preparations). Examples include chitosan, phenoxyethanol and chlorhexidine gluconate. 5-Chloro-2-(2,4-dichlorophenoxy)-phenol (Irgasan®, Ciba Specialty Chemicals Inc.) has also proved especially effective.

As anti-dandruff agents there may be used, for example, climbazole, octopirox and zinc pyrithione. Customary film formers include, for example, chitosan, microcrystalline chitosan, quaternised chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds. As swelling agents for aqueous phases there may be used montmorillonites, clay mineral substances, Pemulen and also alkyl-modified types of Carbopol (Goodrich). Further suitable polymers and swelling agents can be found in the review by R. Lochhead in Cosm. Toil. 108, 95 (1993).

In addition to the primary light-protective substances it is also possible to use secondary light-protective substances of the antioxidant kind which interrupt the photochemical reaction chain triggered when UV radiation penetrates the skin or hair. Typical examples of such anti-oxidants are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, γ-linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts) and also sulfoximine compounds (e.g. buthionine sulfoximines, homocysteine sulfoximine, buthionine sulfones, penta-, hexa- or heptathionine sulfoximine) in very small tolerable amounts (e.g. from pmol to μmol/kg), also (metal) chelating agents (e.g. α-hydroxy fatty acids, palmitic acid phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, α-glycosylrutin, ferulic acid, furfurylidene glucitol, carnosine, butyl hydroxytoluene, butyl hydroxyanisole, nordihydroguaiaretic acid, nordihydroguaiaretic acid, trihydroxybutyrophenone, uric acid and derivatives thereof, mannose and derivatives thereof, superoxide dismutase, N-[3-(3,5-di-tert-butyl-4-hydroxyphenyl)propionyl]sulfanilic acid (and salts thereof, for example the sodium salts), zinc and derivatives thereof (e.g. $ZnO$, $ZnSO_4$), selenium and derivatives thereof (e.g. selenium methionine), stilbene and derivatives thereof (e.g. stilbene oxide, trans-stilbene oxide) and the derivatives suitable according to the invention (salts, esters, ethers, sugars, nucleotides, nucleosides, peptides and lipids) of those mentioned active ingredients. HALS (="Hindered Amine Light Stabilizers") compounds may also be mentioned. The amount of antioxidants present is usually from 0.001 to 30% by weight, preferably from 0.01 to 3% by weight, based on the weight of the UV absorber(s).

To improve the flow behaviour it is also possible to employ hydrotropic agents, for example ethanol, isopropyl alcohol or polyols. The polyols that come into consideration for that purpose have preferably from 2 to 15 carbon atoms and at least two hydroxyl groups. The polyols may also contain further functional groups, especially amino groups, and/or may be modified with nitrogen. Typical examples are as follows:

glycerol;

alkylene glycols, for example ethylene glycol, diethylene glycol, propylene.glycol, butylene glycol, hexylene glycol and also polyethylene glycols having an average molecular weight of from 100 to 1000 Dalton;

technical oligoglycerol mixtures having an intrinsic degree of condensation of from 1.5 to 10, for example technical diglycerol mixtures having a diglycerol content of from 40 to 50% by weight;

methylol compounds, such as, especially, trimethylolethane, trimethylolpropane, trimethylolbutane, pentaerythritol and dipentaerythritol;

lower alkyl-glucosides, especially those having from 1 to 8 carbon atoms in the alkyl radical, for example methyl and butyl glucoside;

sugar alcohols having from 5 to 12 carbon atoms, for example sorbitol or mannitol;

sugars having from 5 to 12 carbon atoms, for example glucose or saccharose;

amino sugars, for example glucamine;

dialcohol amines, such as diethanolamine or 2-amino-1, 3-propanediol.

Suitable preservatives include, for example, phenoxyethanol, formaldehyde solution, Parabens, pentanediol or sorbic acid and the further substance classes listed in Schedule 6, Parts A and B of the Cosmetics Regulations.

Perfume oils that may be mentioned include mixtures of natural and/or synthetic aromatic substances. Natural aromatic substances are, for example, extracts from blossom (lilies, lavender, roses, jasmine, neroli, ylang-ylang), from stems and leaves (geranium, patchouli, petitgrain), from fruit (aniseed, coriander, carraway, juniper), from fruit peel (bergamot, lemons, oranges), from roots (mace, angelica, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come into consideration, for example civet and castoreum. Typical synthetic aromatic substances are, for example, products of the ester, ether, aldehyde, ketone, alcohol or hydrocarbon type. Aromatic substance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, α-isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, dihydromyrcenol, lilial, lyral, citronellol, phenyl ethyl alcohol, α-hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, β-damascone, bourbon geranium oil, cyclohexyl salicylate, vertofix coeur, iso-E-Super, Fixolide NP, evernyl, iraldein gamma, phenylacetic acid, geranyl acetate, benzyl acetate, rose oxide, romillat, irotyl and floramat alone or in admixture with one another.

There may be used as colorants the substances that are suitable and permitted for cosmetic purposes, as compiled, for example, in the publication "Kosmetische Färbemittel" of the Farbstoffkommission der Deutschen Forschungsgemeinschaft, Verlag Chemie, Weinheim, 1984, pages 81 to 106. The colorants are usually used in concentrations of from 0.001 to 0.1% by weight, based on the total mixture.

Typical examples of bacteria-inhibiting agents are preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% by weight, based on the solids content of the preparations.

It is furthermore possible for the cosmetic preparations to contain, as adjuvants, anti-foams, such as silicones, structurants, such as maleic acid, solubilizers, such as ethylene glycol, propylene glycol, glycerol or diethylene glycol, opacifiers, such as latex, styrene/PVP or styrene/acrylamide copolymers, complexing agents, such as EDTA, NTA, β-alaninediacetic acid or phosphonic acids, propellants, such as propane/butane mixtures, $N_2O$, dimethyl ether, $CO_2$, $N_2$ or air, so-called coupler and developer components as oxidation dye precursors, reducing agents, such as thioglycolic acid and derivatives thereof, thiolactic acid, cysteamine, thiomalic acid or α-mercaptoethanesulfonic acid, or oxidising agents, such as hydrogen peroxide, potassium bromate or sodium bromate.

There come into consideration as insect repellents, for example, N,N-diethyl-m-toluamide, 1,2-pentanediol or insect repellent 3535; suitable self-tanning agents are, for example, dihydroxyacetone, erythrulose or mixtures of dihydroxyacetone and erythrulose.

Cosmetic formulations according to the invention are contained in a wide variety of cosmetic preparations. There come into consideration, for example, especially the following preparations:

skin-care preparations, e.g. skin-washing and cleansing preparations in the form of tablet-form or liquid soaps, soapless detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or perfume creams;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hairsetting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidising dyes, or natural hair colorants, such as henna or camomile.

The final formulations listed may exist in a wide variety of presentation forms, for example:

in the form of liquid preparations as a W/O, O/W, O/W/O, W/O/W or PIT emulsion and all kinds of microemulsions, in the form of a gel, in the form of an oil, a cream, milk or lotion, in the form of a powder, a lacquer, a tablet or make-up, in the form of a stick, in the form of a spray (spray with propellant gas or pump-action spray) or an aerosol, in the form of a foam, or in the form of a paste.

Of special importance as cosmetic preparations for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection oils, sun protection milk and sun protection preparations in the form of a spray.

Of special importance as cosmetic preparations for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition: from 0.01 to 5% by weight of a UV absorber according to the invention, 12.0% by weight of sodium laureth-2-sulfate, 4.0% by weight of cocamidopropyl betaine, 3.0% by weight of sodium chloride, and water ad 100%.

For example, especially the following hair-cosmetic formulations may be used:

$a_1$) spontaneously emulsifying stock formulation, consisting of the UV absorber according to the invention, PEG-6-$C_{10}$oxoalcohol and sorbitan sesquioleate, to which water and any desired quaternary ammonium compound, for example 4% minkamidopropyl di-methyl-2-hydroxyethylammonium chloride or Quaternium 80, is added;

$a_2$) spontaneously emulsifying stock formulation consisting of the UV absorber according to the invention, tributyl citrate and PEG-20-sorbitan monooleate, to which water and any desired quaternary ammonium compound, for example 4% minkamidopropyl di-methyl-2-hydroxyethylammonium chloride or Quaternium 80, is added;

b) Quat-doped solutions of the UV absorber according to the invention in butyl triglycol and tributyl citrate;

c) mixtures or solutions of the UV absorber according to the invention with n-alkylpyrrolidone.

The following Examples illustrate the invention but do not limit the invention thereto.

EXAMPLES OF THE PREPARATION OF THE SLN SUSPENSION

Determination of Particle Size

The particle size is determined by dynamic light scattering (photon correlation spectroscopy). An ALV system (DLS 5000) with a frequency-doubled Nd-YAG laser (Uniphase, output 50 mW) is used for that purpose. The autocorrelation function is measured at a scattering angle of 90° and matched with a second order cumulant fit from which the hydrodynamic diameter and the polydispersity index can then be derived.

In Vitro Determination of the Sun Protection Factor (SPF)

The in vitro SPF values are measured using an Optometrix 290 SPF analyzer in accordance with the method described by Diffey and Robson (B. L. Diffey, J. Robson, *J. Soc. Cosmet Chem.* 40 (1989) 127–133). Transpore™ tape (3M) affixed to quartz plates is used as the substrate.

Example 1

SLN Suspension Containing 2% BEMT

A nanosuspension with a 2% content of the compound of formula

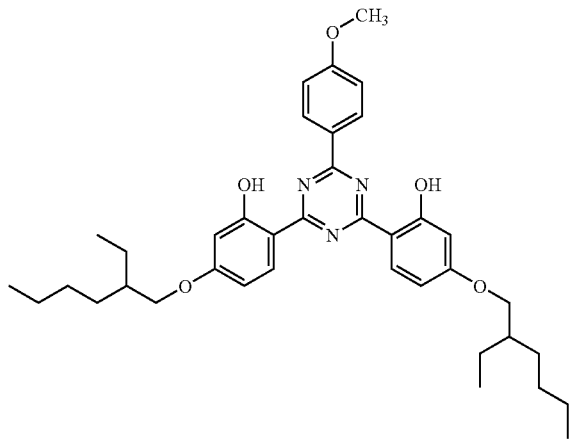

(101)

(bisethylhexyloxyphenol methoxyphenyl triazine (BEMT)) is prepared.

For that purpose, first of all 40 g of glycerol trimyristate and 5 g of caprylyl pyrrolidone are heated to 85° C. and mixed. 5 g of the compound of formula (101) are then added to that mixture.

200 g of a 5% aqueous solution of Phospholipon 80 are likewise heated to 85° C. The two solutions are then combined and mixed together using an Ultraturrax, and subsequently homogenized using a high-pressure homogenizer and then cooled.

A suspension having an SLN content of 20% is thereby obtained.

The proportion of UV absorber in the particles is 10%, resulting in a concentration of the UV absorber in the formulation of 2%. The particle size determined by means of photon correlation spectroscopy is 210 nm with a polydispersity index of 0.18.

A value of 5 is ascertained for the in vitro SPF.

Example 2

SLN Suspension Containing 4% DBT

A nanosuspension with a 4% content of DBT is prepared. For that purpose, first of all 35 g of cetyl palmitate and 5 g of octocrylene are heated to 85° C. and mixed. 10 g of DBT are then added to the resulting mixture. 200 g of a 5% aqueous solution of coco glucoside are likewise heated to 85° C. The two solutions are then combined and mixed together using an Ultraturrax, and subsequently homogenized using a high-pressure homogenizer and then cooled.

A suspension having an SLN content of 20% is thereby obtained. The proportion of UV absorber in the particles is 20%, resulting in a concentration of the UV absorber in the formulation of 4%. In addition, the UVB absorber octocrylene is present in a concentration of 2%.

The particle size determined by means of photon correlation spectroscopy is 230 nm with a polydispersity index of 0.20. A value of 10 is ascertained for the in vitro SPF.

Example 3

SLN Suspension Containing 4% BEMT

A nanosuspension with a 4% content of BEMT is prepared. For that purpose, first of all 80 g of glycerol tristearate and 10 g of ethylhexyl methoxycinnamate are heated to 85° C. and mixed. 10 g of BEMT are then added to the resulting mixture. 150 g of a 12% aqueous solution of Phospholipon 80 are likewise heated to 85° C. The two solutions are then combined and mixed together using an Ultraturrax, and subsequently homogenized using a high-pressure homogenizer and then cooled.

A suspension having an SLN content of 40% is thereby obtained.

The proportion of UV absorber in the particles is 10%, resulting in a concentration of the UV absorber in the formulation of 4%. In addition, the UVB absorber ethylhexyl methoxycinnamate is present in a concentration of 4%.

The particle size determined by means of photon correlation spectroscopy is 260 nm with a polydispersity index of 0.22.

A value of 16 is ascertained for the in vitro SPF.

Example 4

Sunscreen Formulation with a BEMT-containing SLN Suspension

|   | Components | % |
|---|---|---|
| A | polyglyceryl-3 methylglucose distearate | 2.0 |
|   | decyl oleate | 6.0 |
|   | isopropyl palmitate | 5.0 |
|   | caprylic/capric triglyceride | 6.0 |
|   | octyl triazone | 2.0 |
|   | octocrylene | 5.0 |
|   | butyl methoxy dibenzoyl methane | 1.0 |
| B | SLN suspension from Example 3 | 50.0 |
|   | Phenonip | 0.5 |
|   | water | 21.5 |
| C | carbomer 141 | 0.2 |
|   | isopropyl palmitate | 0.8 |

Phases A and B are separately briefly heated to 70° C. and then mixed together with cautious stirring. Phase C is then added to the resulting mixture of phases A and B, whereupon the resulting mixture is intensively homogenized. The homogenate is cooled to room temperature with gentle stirring.

A value of 23 is ascertained for the in vitro SPF.

What is claimed is:

1. A solid lipid nanoparticle composition containing
   (a) 1 to 40% by weight of an oil-soluble UV absorber,
   (b) 20 to 98.9% by weight of a solid lipid having a diameter of from 10 nm to 10 μm,
   (c) 0.1 to 20% by weight of an emulsifier selected from alkali metal salts, ammonium salts and amine salts of fatty acids, saturated and unsaturated alkylsulfates, salts of bile acid, invert soaps (quats), partial fatty acid esters of sorbitan, sugar esters of fatty acids, alkyl glucosides, alkyl maltosides, betaines, proteins, fatty acid polyglycerol esters; fatty acid propylene glycol esters; fatty acid lactates and fatty alcohol phosphates and (d) 0 to 40% by weight of a liquid lipid or a liquid oil-miscible UV absorber, wherein the oil-soluble UV absorber (a) is dissolved or dispersed in the lipid.

2. A composition according to claim 1, wherein the UV absorber corresponding to component (a) is selected from
   ($a_1$) phenyltriazine derivatives,
   ($a_2$) dibenzoylmethane derivatives,
   ($a_3$) diphenylacrylate derivatives,
   ($a_4$) benzofuran derivatives,
   ($a_5$) polymeric UV absorbers containing one or more organosilicon radicals,
   ($a_6$) camphor derivatives,
   ($a_7$) trianilino-s-triazine derivatives,
   ($a_8$) phenylbenzimidazolesulfonic acid and salts thereof,
   ($a_9$) menthyl anthranilates,
   ($a_{10}$) benzotriazole derivatives,
   ($a_{11}$) triazones,
   ($a_{12}$) trisiloxane compounds and
   ($a_{13}$) the compound of formula

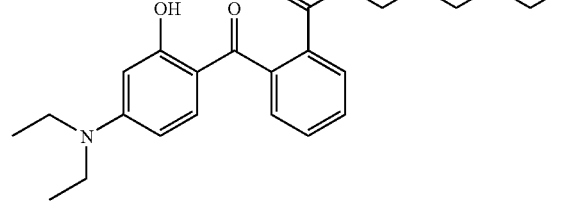

3. A composition according to claim 2, wherein the UV absorber corresponding to component (a) is selected from
   ($a_1$) p-aminobenzoic acid derivatives,
   ($a_{10}$) phenyltriazine derivatives,
   ($a_2$) dibenzoylmethane derivatives,
   ($a_8$) camphor derivatives,
   ($a_{15}$) triazones and
   ($a_{16}$) trisiloxane compounds.

4. A composition according to claim 2, wherein the UV absorber corresponding to component ($a_1$) corresponds to formula

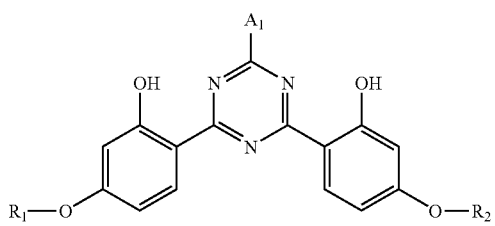

(1)

wherein
$R_1$ and $R_2$ are each independently of the other $C_3$–$C_{18}$alkyl; $C_2$–$C_{18}$alkenyl; or a radical of formula —$CH_2$—CH(—OH)—$CH_2$—O—$T_1$; or
$R_1$ and $R_2$ are a radical of formula (4a)

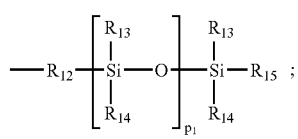

$R_{12}$ is a direct bond; a straight-chain or branched $C_1$–$C_4$alkylene radical, or a radical of formula —$C_{m_1}H_{2m_1}$— or —$C_{m_1}H_{2m_1}$—O—;

$R_{13}$, $R_{14}$ and $R_{15}$ are each independently of the others $C_1$–$C_{18}$alkyl; $C_1$–$C_{18}$alkoxy or a radical of formula

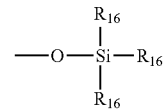

$R_{16}$ is $C_1$–$C_5$alkyl;
$m_1$ and $m_3$ are each independently of the other from 1 to 4;
$P_1$ is 0 or a number from 1 to 5;
$A_1$ is a radical of formula

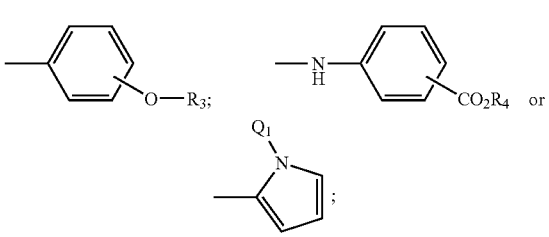

$R_3$ is hydrogen; hydroxy; $C_1$–$C_{10}$alkyl, —($CH_2CHR_5$—O)$_{n_1}$—$R_4$; or a radical of formula —$CH_2$—CH(—OH)—$CH_2$—O—$T_1$;
$R_4$ is hydrogen; M; $C_1$–$C_5$alkyl; or a radical of formula —($CH_2$)$_{m_2}$—O—$T_1$;
$R_5$ is hydrogen; or methyl;
$T_1$ is hydrogen; or $C_1$–$C_8$alkyl;
$Q_1$ is $C_1$–$C_{18}$alkyl;
M is a metal cation;
$m_2$ is from 1 to 4; and
$n_1$ is from 1 to 16.

5. A composition according to claim 2, wherein the UV absorber corresponding to component ($a_1$) corresponds to formula

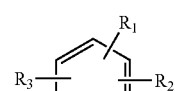

(2)

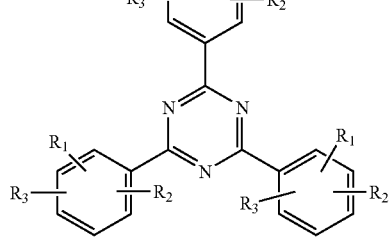

wherein
$R_1$ and $R_2$ are each independently of the others hydrogen; $C_1$–$C_{12}$alkyl; or $C_1$–$C_{12}$alkoxy; and
$R_3$ is $C_1$–$C_{12}$alkyl; or $C_1$–$C_{12}$alkoxy.

6. A composition according to claim 1, wherein component (b) is selected from cetyl palmitate, glycerol trilaurate, glycerol tristearate, glycerol trimyristate, glycerol tripalmitate, glycerol tribehenate, glycerol behenate, stearic acid, cholesterol, beeswax and the $C_{16}$–$C_{18}$ fatty acids of mono-, di- and tri-glycerides.

7. A composition according to claim 1, wherein component (d) is present and is selected from caprylic/capric triglycerides and from ethylhexylmethoxy cinnamate present in the form of an oil, octocrylene and Parsol SLX.

8. A composition according to claim 1 which, in addition, comprises dispersion-stabilizing additives.

9. A composition according to claim 1 which comprises, as dispersion-stabilizing additives, surfactants, sterically stabilizing substances or viscosity-increasing substances.

10. A composition according to claim 4 which comprises
 (a) a UV absorber of formula (1)
 (b) a synthetic mono-, di- or tri-glyceride, and
 (c) a fatty alcohol phosphate.

11. A composition according to claim 2 which comprises
 (a) as UV absorber, butamidotriazone,
 (b) a synthetic mono-, di- or tri-glyceride, and
 (c) a fatty alcohol phosphate.

12. A cosmetic skin or hair preparation, comprising a solid lipid nanoparticle composition according to claim 1,
 and also carriers or adjuvants acceptable in skin and hair cosmetics.

* * * * *